United States Patent [19]
Bonelli et al.

[11] Patent Number: 5,126,024
[45] Date of Patent: Jun. 30, 1992

[54] APPARATUS AND METHOD FOR CONCENTRATING MICROORGANISMS FROM A LIQUID MEDIUM ON AN ELECTRODE BY ELECTRODEPOSITION

[75] Inventors: Joseph E. Bonelli, Boulder, Colo.; Louis M. Fink, Little Rock, Ark.; Kent J. Voorhees, Golden, Colo.

[73] Assignee: Colorado School of Mines, Golden, Colo.

[21] Appl. No.: 452,816

[22] Filed: Dec. 19, 1989

[51] Int. Cl.⁵ .............. C25D 13/00; B01D 61/42; B01D 57/02
[52] U.S. Cl. ............... 204/180.2; 204/299 R; 204/180.1; 204/181.4
[58] Field of Search ............ 204/182.8, 180.2, 181.4, 204/180.1, 299 R

[56] References Cited
U.S. PATENT DOCUMENTS 3,839,175  10/1974  Keyes .................. 204/299 R
4,764,473  8/1988  Matschke ............... 204/272

Primary Examiner—John Niebling
Assistant Examiner—Caroline Koestner
Attorney, Agent, or Firm—J. Winslow Young

[57] ABSTRACT

An apparatus and method for the electrodeposition of microorganisms on an electrode using a weak, direct current voltage. The electrodeposition of the microorganisms occurs within a relatively short period of time thereby reducing the requirement for culturing the microorganisms. The electrode can be used as an electrode for a Curie point pyrolysis mass spectrometer to determine the specific microorganism electrodeposited on the electrode.

15 Claims, 9 Drawing Sheets

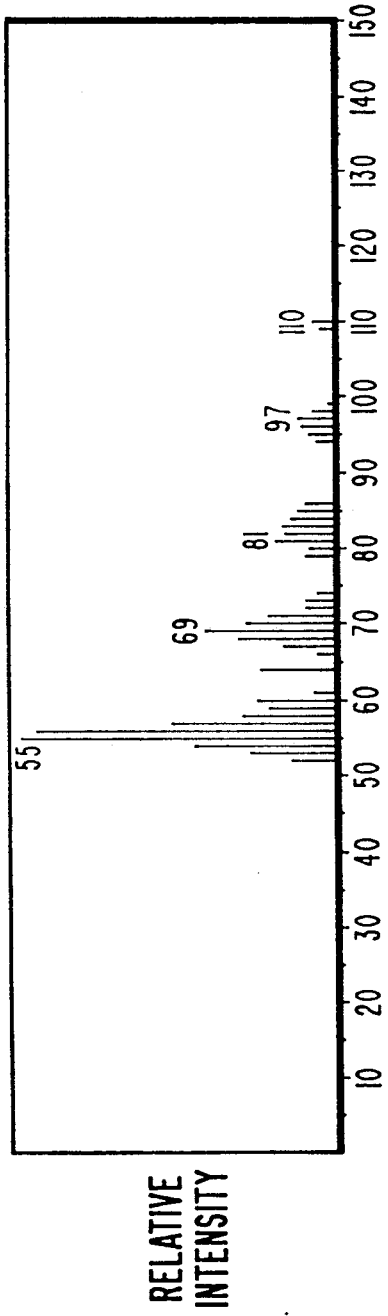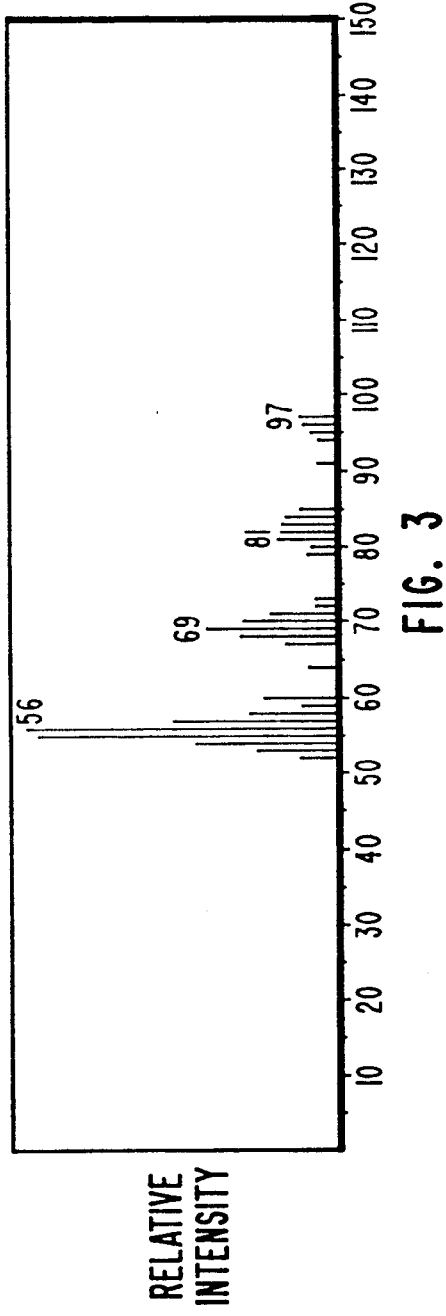

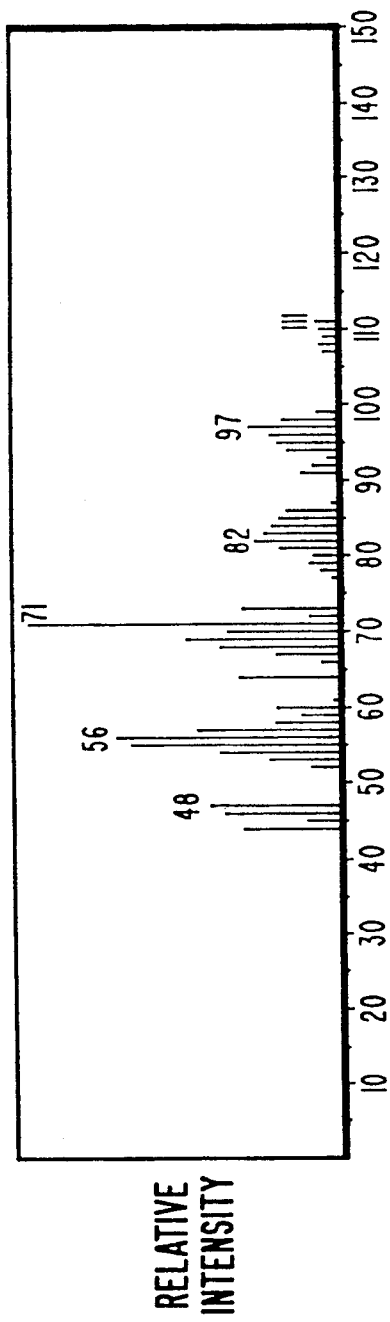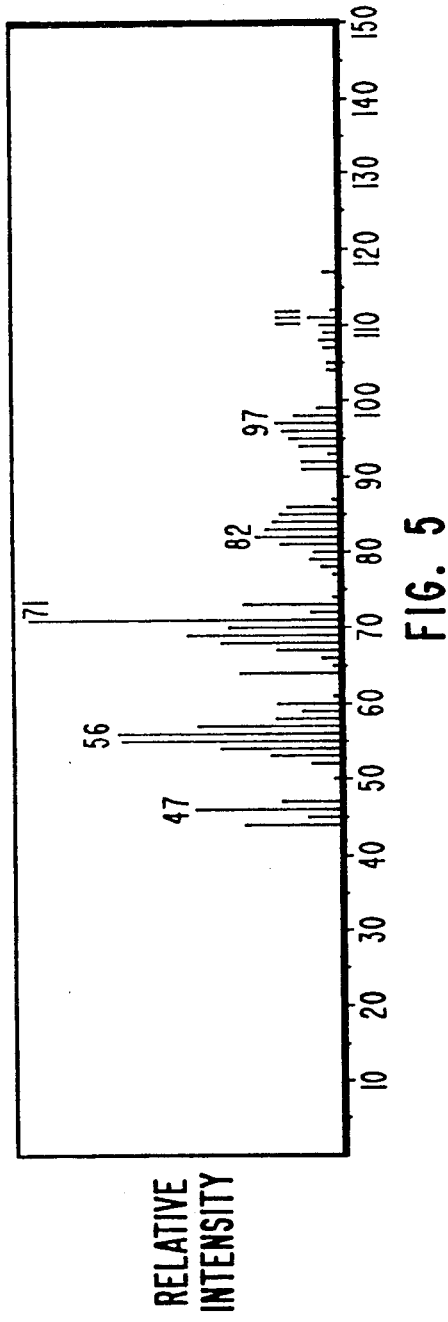

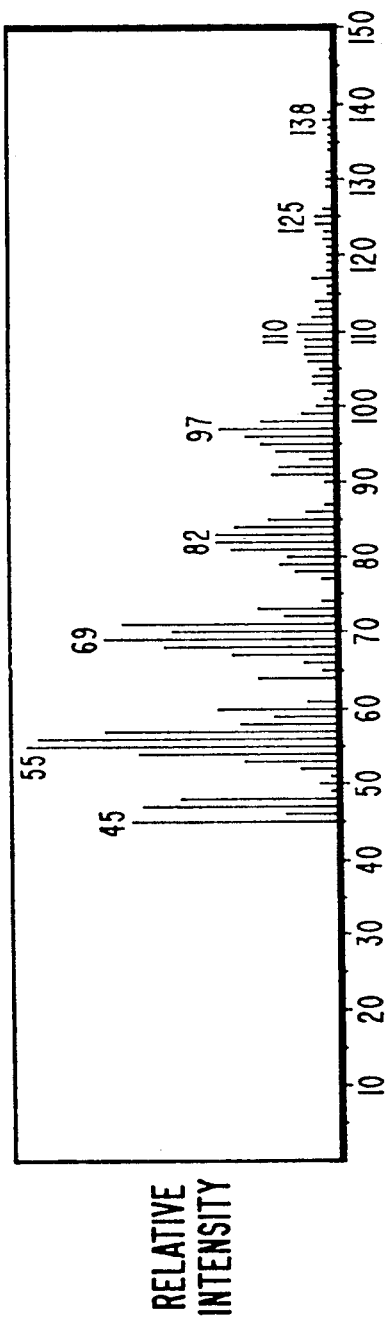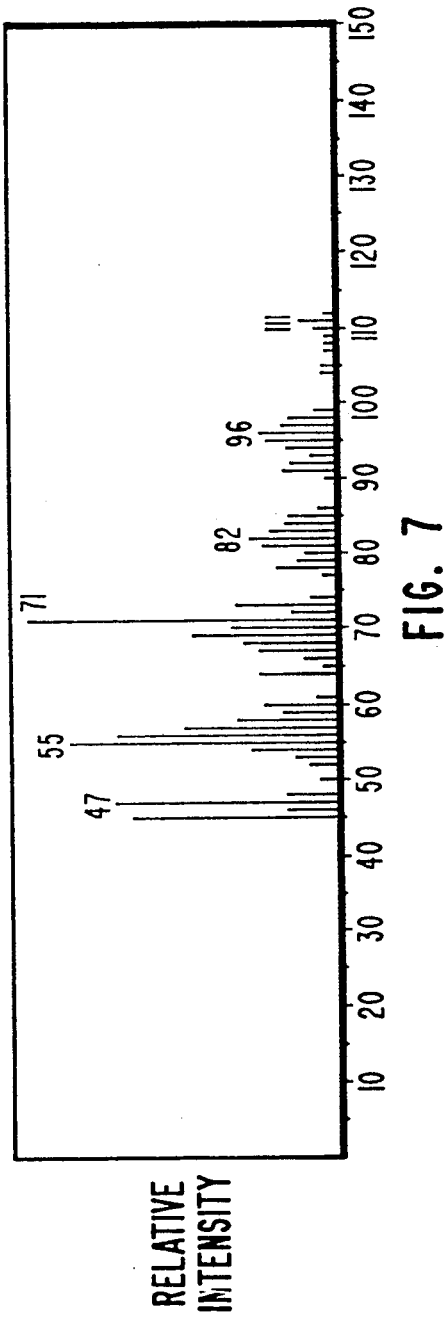

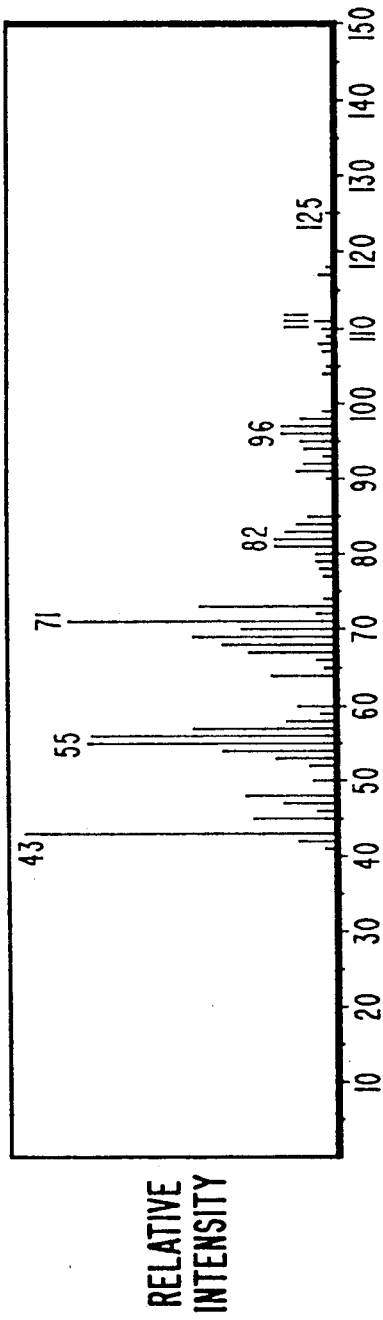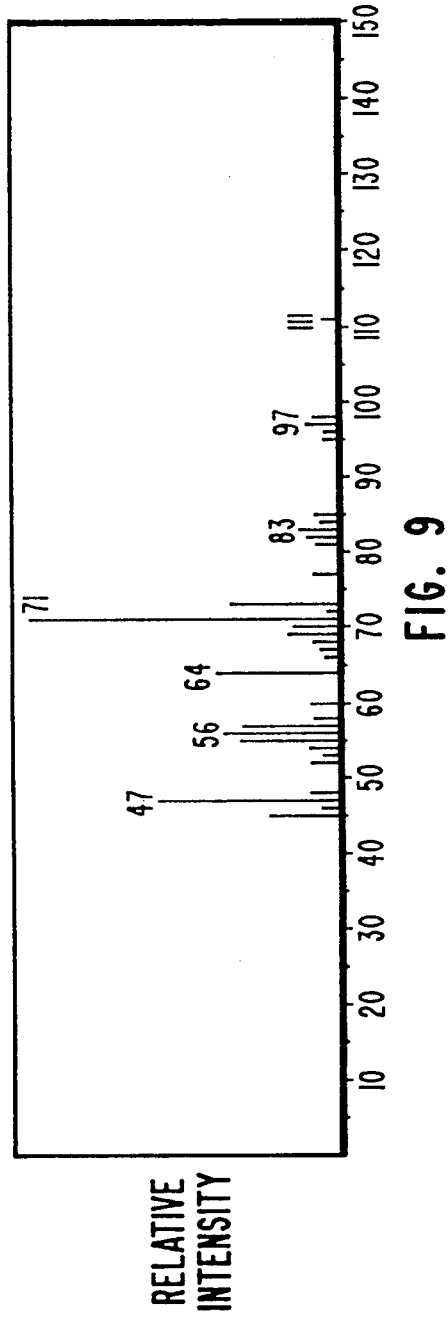

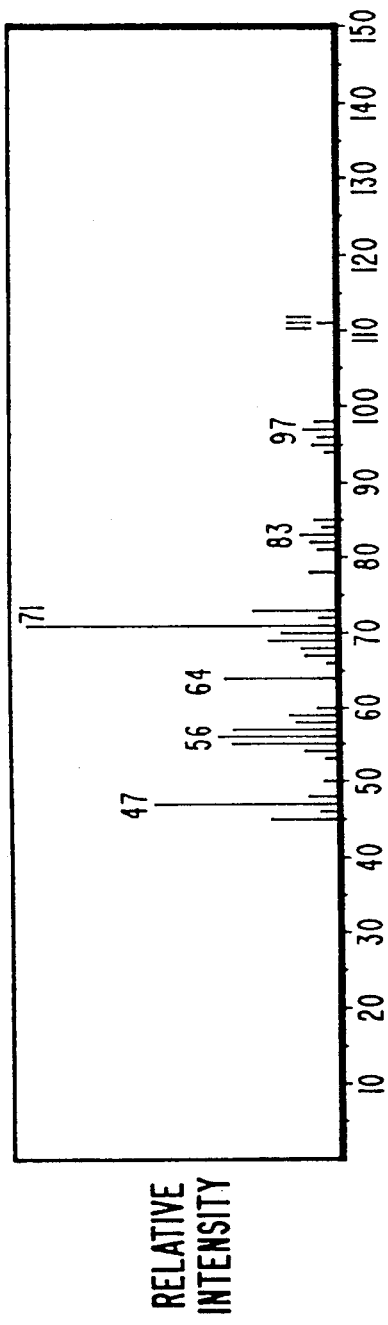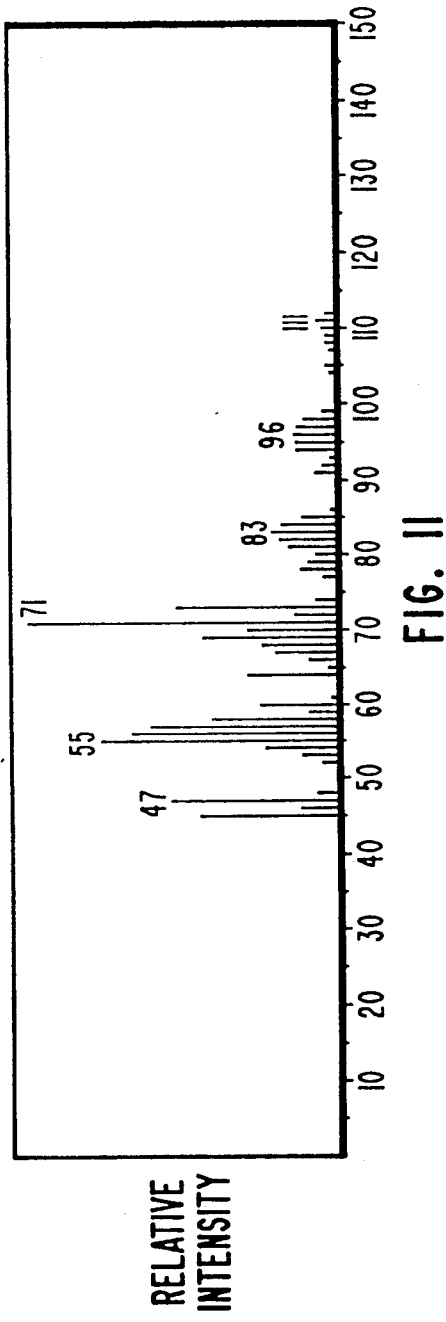

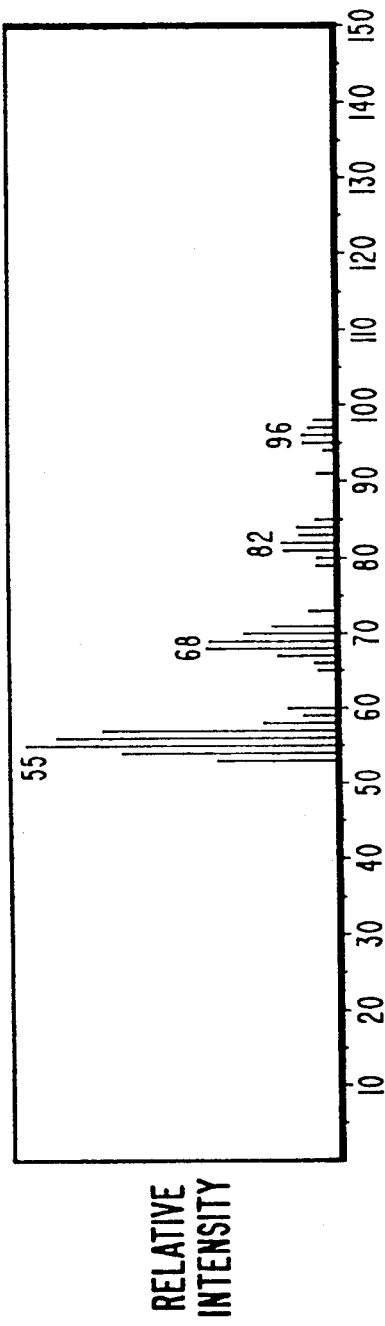
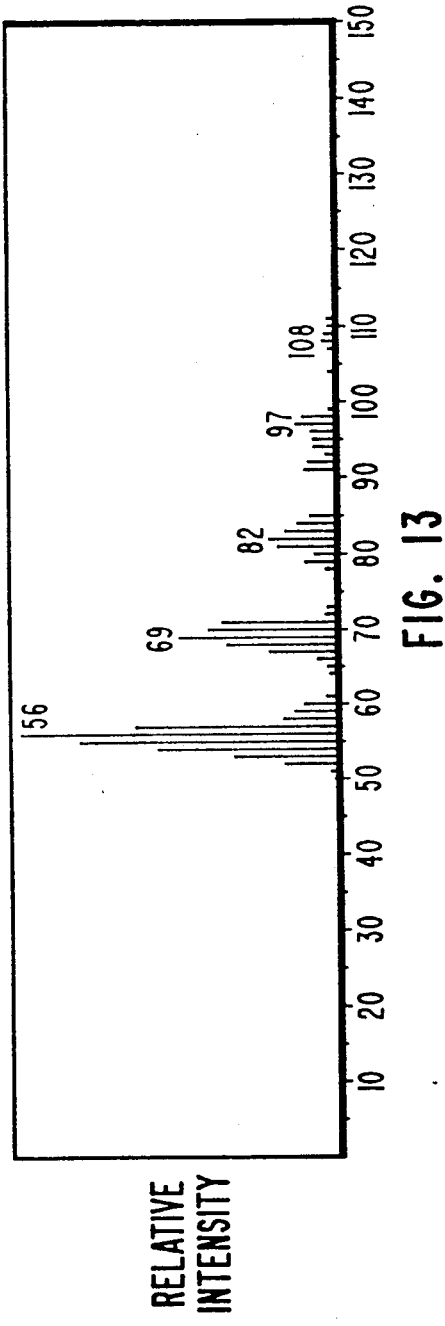

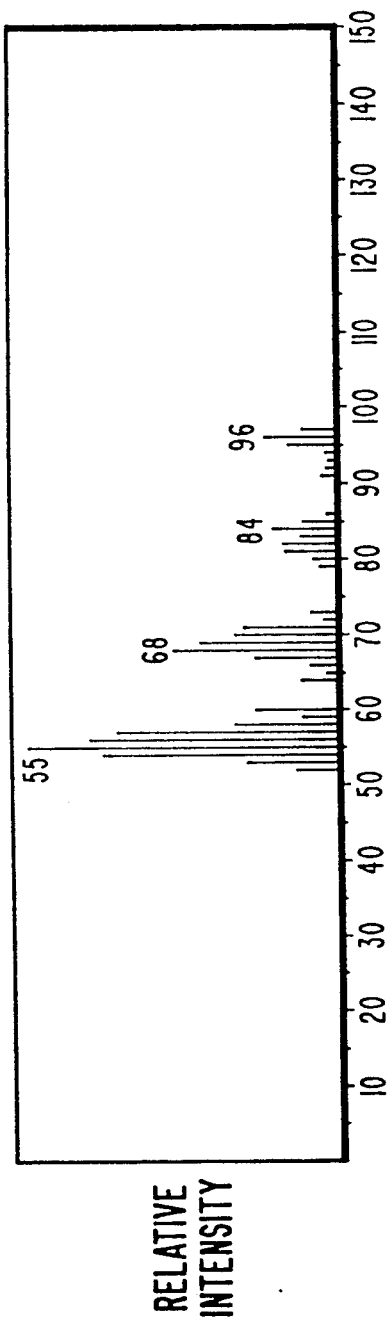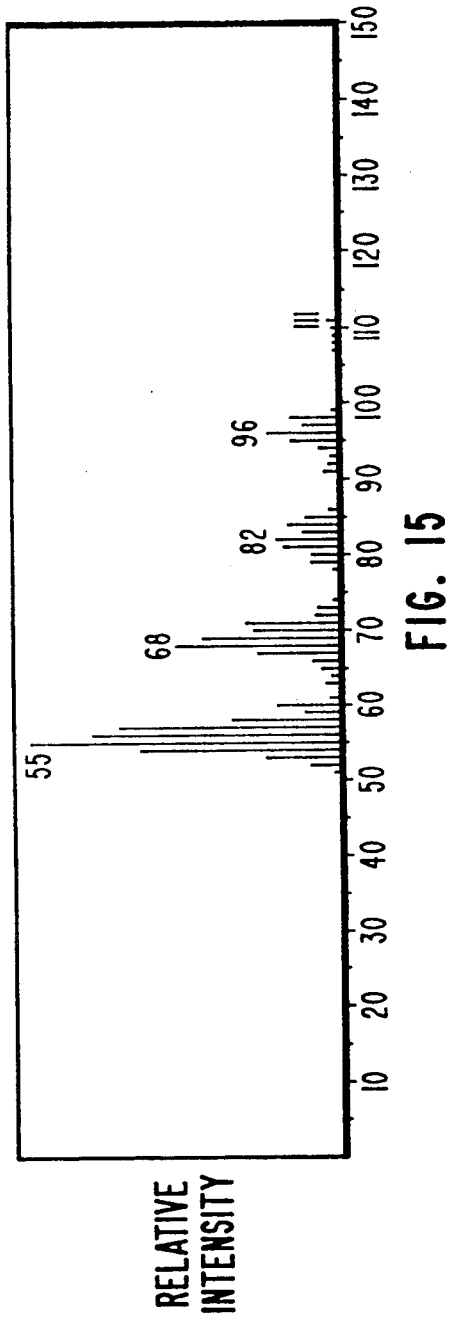

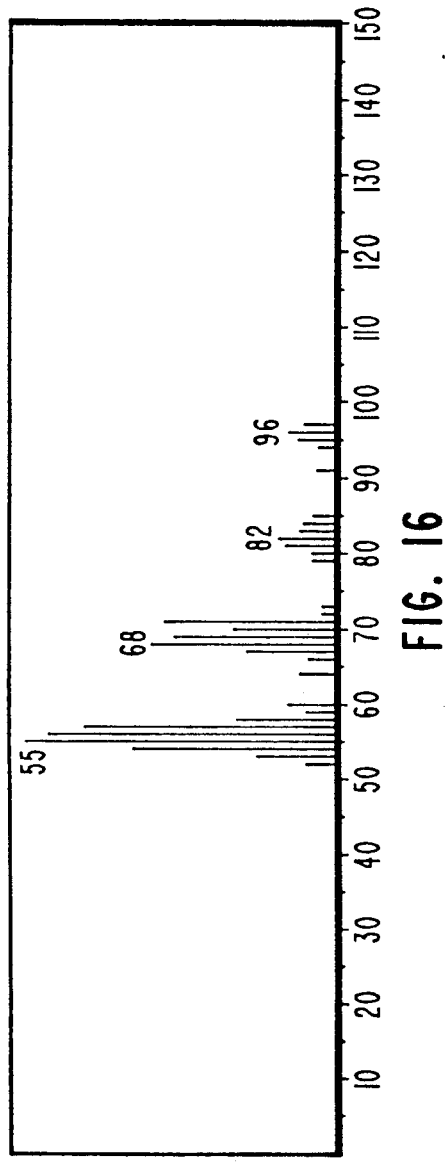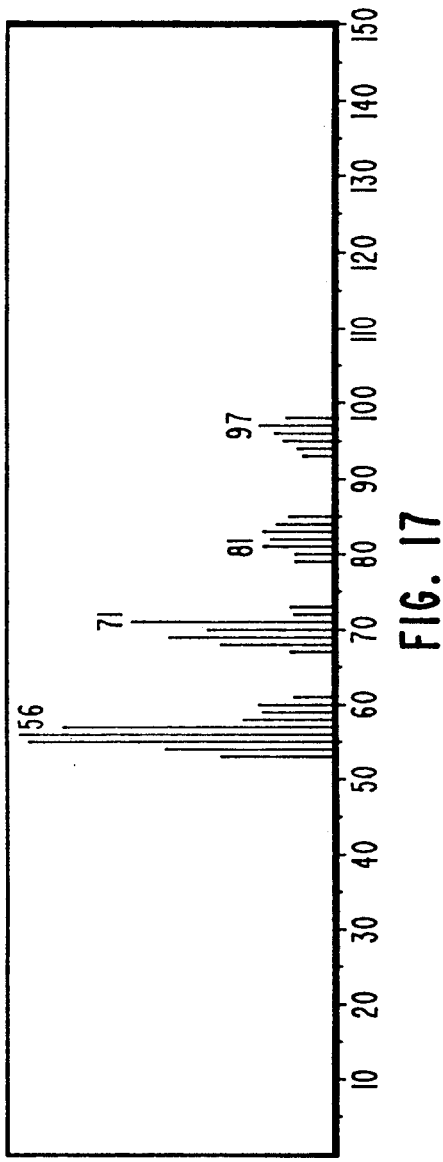

APPARATUS AND METHOD FOR CONCENTRATING MICROORGANISMS FROM A LIQUID MEDIUM ON AN ELECTRODE BY ELECTRODEPOSITION

Background

1. Field of the Invention

This invention relates to an apparatus and method for concentrating microorganisms in a liquid medium and, more particularly, to an apparatus and method for concentrating microorganisms in a liquid medium on the tip of a probe of a pyrolysis mass spectrometer using a weak, direct current voltage with the probe serving as the anode.

2. The Prior Art

Microorganisms, such as bacteria, fungi, yeasts, and viruses, to name several, are economically important in many aspects of life ranging between those essential for food production to those responsible for diseases. Most microorganisms require a liquid medium in order to be viable but are present usually in a fairly low concentration dispersed throughout the liquid medium. Widely dispersed or dilute concentrations of microorganisms are difficult to detect, analyze, or otherwise collect or harvest without elaborate additional steps. For example, certain disease-causing microorganisms are present in the urine but in such low concentrations that additional culturing is required. Culture times range between several hours to several days so that the required culture time can result in an unacceptable delay prior to being able to initiate the appropriate treatment. Further, in certain circumstances, more than one species of microorganism may be present in the biological medium and the culture procedure could favor the growth of a first microorganism over a second microorganism with the result that rapid growth of the first microorganism will mask the presence of the second microorganism.

The imposition of an electric field on microorganisms in a liquid medium has been studied and implemented for various applications. A number of references are available which teach the use of an electric field to sequester microorganisms, control their growth rate, and induce cell infusion. Several of these patents are noted and discussed below:

Schaefer, et al. (U.S. Pat. No. 3,133,003) discloses a method for controlling the growth rate of microorganisms by subjecting the microorganism to an atmosphere having a preponderance of artificially created negative ions.

Goldner (U.S. Pat. No. 3,266,943) discloses a process for inoculating a metallic electrode which is to be used to form a bio-electrode. The process includes dispersing a finely divided iron powder throughout the culture medium for a time sufficient to permit substantial growth of the bacteria on the finely divided particles. A magnetic field is then used to attract the particles to the electrode thus carrying the bacteria to the electrode.

Hofmann (U.S. Pat. No. 4,561,961) discloses an apparatus for use in a live cell fusion system including a pair of hollow, tubular electrodes. Cells in a fluid medium, when exposed to electric field, generally behave like uncharged particles suspended in a liquid. The field induces charge separation in the cells. An alternating electric field can be used to move cells in one direction. When the cells come closer to the area of field concentration, they start being attracted to each other and form pearl chains of two or more cells.

Hoffmann (U.S. Pat. No. 4,578,168) discloses an apparatus for performing electro cell fusion on a large scale basis. An alternating electric field is used to move the cells in one direction so that when the cells come in closer to the area of the field of concentration they start being attracted to each other and form pearl chains of two or more cells. A single wire electrode is supported in a fusion chamber defined by a heavy metal cylinder.

Sowers (U.S. Pat. No. 4,622,302) discloses an apparatus and process for inducing membrane fusion under an electric field. Pulses of direct current at specific pulse rates and electric field strength are applied to the membrane suspension causing the fusogenic membranes to come in contact with each other.

Arnold, et al. (U.S. Pat. No. 4,634,669) discloses a process for facilitating the differentiation of particles in a medium. The particles are exposed to a rotating electric field of variable rotational frequency. The frequency of the rotating field is adjusted to a frequency at which the particles to be differentiated rotate in different directions.

Hansen (U.S. Pat. No. 4,661,451) discloses an apparatus for immobilizing biological cells based on the dielectric properties of the biological cells. Cells, when placed in an inhomogeneous electric field generated by an alternating current source experience a net force in the direction of the field source. By arranging an array of grid points having the numerical density desired to attract and immobilize the number of cells required for analysis in a desired pattern and by connecting the same to an inhomogeneous field generating source, one may vastly simplify cell locating operations since the positions of the cells will now be associated with a grid point location.

Hilliard, et al. (U.S. Pat. No. 4,695,547) discloses an electrode structure for treating samples of genetic material in a well tray. The electrode structure includes an outer electrode in the form of a metal ring having a diameter just slightly less than the inner diameter of the sample well and a center electrode in the form of a metal rod.

Matschke (U.S. Pat. No. 4,699,881) discloses an apparatus for the treatment of biological cells with an electric field. The surfaces of the electrodes are positioned so as to provide a uniform spatial separation between the electrodes so that the electric field strength is equal thereby subjecting all the cells found between the electrodes to the same electrical conditions.

Matschke, et al. (U.S. Pat. No. 4,764,473) discloses a chamber for the treatment of cells in an electric field in which a space formed by electrically nonconducting walls is provided to hold the suspension containing the cells. At least two electrodes are extended into the space in such a way that a region bounded by them is formed between electrodes so that the cells passing between the electrodes are exposed to an electrical field developed between the electrodes.

It should be carefully noted from each of the foregoing references that the electrical field called for is an alternating, poorly homogeneous field, and, further, that none of these references incorporate a direct current voltage imposed on the liquid medium to concentrate the microorganisms.

In view of the foregoing, it would be an advancement in the art to provide an apparatus and method for concentrating microorganisms from a liquid medium utilizing a weak, direct current voltage. It would also be another advancement in the art to utilize an electrode from a pyrolysis mass spectrometer as an anode upon which microorganisms are concentrated. Such a novel apparatus and method is disclosed and claimed herein.

BRIEF SUMMARY AND OBJECTS OF THE INVENTION

This invention involves the concentration of microorganisms in a liquid medium by imposing a weak, direct current voltage on the liquid medium. One of a pair of electrodes is used as the anode, the tips of which are immersed in the liquid. A weak, (less than about 20 volts) direct current voltage is imposed on the liquid medium resulting in the electrodeposition of the microorganisms on the electrode serving as the anode. The liquid medium can be from any suitable source such as body fluids, culture media, water treatment systems, and the like.

It is, therefore, a primary object of this invention to provide improvements in apparatus for concentrating microorganisms in a liquid medium.

Another primary object of this invention is to provide improvements in the method of concentrating microorganisms in a liquid medium.

Another object of this invention is to provide an apparatus for the electrodeposition of microorganisms from a liquid medium.

Another object of this invention is to provide an apparatus for the electrodeposition of microorganisms on an electrode that can then be processed in a pyrolysis mass spectrometer.

These and other objects and features of the present invention will become more readily apparent from the following description in which preferred and other embodiments of the invention have been set forth in conjunction with the accompanying drawing and appended claims.

BRIEF DESCRIPTION OF THE DRAWING

FIGS. 2-17 are spectra of various bacterial samples obtained with a pyrolysis mass spectrometer.

DETAILED DESCRIPTION OF THE PREFERRED EMBODIMENT

General Discussion

Figure 1:
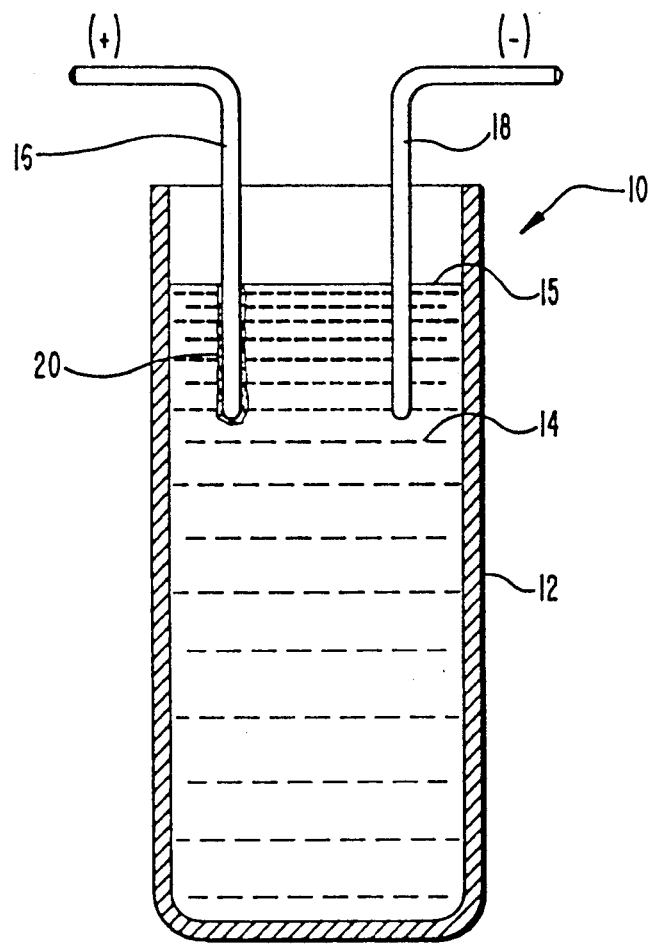
FIG. 1 is a cross sectional, schematic illustration of one presently preferred embodiment of this invention.

All microorganisms, whether bacteria, fungi or viruses contain many weakly acidic or basic functional groups in their proteins, glycoproteins, and polysaccharides exposed to the external environment. Additionally, a slight separation of electrical charge is maintained inside the microorganism between the internal and the external environments as a consequence of metabolic activity, homeostasis, and requirements of motility. We have discovered that the resulting net, nonzero electrical charge on individual microorganisms causes them, by means which are yet not clearly understood, to be attracted to charged surfaces such as wires or foils. Under relatively mild conditions of electrolysis (1-20 volt direct current) large numbers of bacteria have been successfully immobilized and concentrated on the surfaces of wires as determined by fluorescent staining and pyrolysis mass spectrometry of the deposited residue.

One goal of the research that created this invention was to electrodeposit bacteria on the tip of a ferromagnetic wire which could then be used as a heating filament in a pyrolysis mass spectrometer to analyze the bacteria so collected. The bacteria used were both live and killed bacteria and included *Escherichia coli*, Group B Streptococcus, Wolinella species, and *Wolinella succinogenes*.

The *Escherichia coli* and Group B Streptococcus bacteria were obtained from a general hospital in the local community. The *Escherichia coli* and Group B Streptococcus bacteria experiments were performed with initially live bacteria. The Wolinella bacteria was obtained as left over product from an experiment by another researcher. All killed bacteria were obtained by thorough autoclaving.

The live bacteria were prepared by removing an aliquot from the original test tube and transferring it to a 20 ml centrifuge tube. The bacteria were then washed three times with deionized water and processed with a centrifuge prior to being deposited in the cell. The killed bacteria were added straight to the cell.

The amount of bacteria used in the cell was a relative amount determined by the volume of the original aliquot taken which ranged from 0.5 ml to 2.0 ml. The cell was either a 20 ml or 10 ml pyrex beaker. The washed bacteria were added to the cell and then diluted with deionized water to approximately 17 ml or 8 ml, respectively. If stirring was desired, a small stir plate was placed under the cell causing the ferromagnetic wire electrodes to vibrate thereby stirring the solution vigorously.

A low voltage power supply was used in the experiment and had a maximum voltage of 22 volts of direct current. For these experiments the amperage was not monitored closely but never rose above about 0.1 amps. The two leads were supported by a bar attached to a ring stand and connected directly to the ferromagnetic wires.

Detailed Description

Referring now specifically to FIG. 1, a schematic representation of the novel apparatus for concentrating microorganisms from a liquid medium on the tip of an electrode which can be used as a heating filament for a pyrolysis mass spectrometer is shown generally at 10 and includes a vessel 12 containing a liquid medium 14 therein and into which the tips of electrodes 16 and 18 are inserted. Electrodes 16 and 18 are immersed a short distance into liquid medium 14 as measured from the upper surface 15. We have found that immersion of electrodes 16 and 18 to a depth of about 2.0 centimeters or less is sufficient to obtain an adequate concentration of microorganisms on the anode, electrode 16, as shown schematically herein as microorganisms 20.

Experimental Procedure

In the cell or vessel 12, two ferromagnetic wires (electrodes 16 and 18) were connected to the leads of the power supply, as indicated schematically by the positive sign (+) on electrode 16 and the negative sign (−) on electrode 18, and placed in vessel 12 approximately two centimeters deep below surface 15 of liquid 14. Power was supplied for a period of time ranging between ten minutes and two hours. The optimum time seemed to be about thirty minutes. The voltage supplied ranged from one to twenty volts.

After the electrodeposition was completed, the wire that served as the anode or positive electrode 16 was removed for analysis on the pyrolysis mass spectrometer. As many as four electrodeposited wires, electrode 16 with microorganisms 20 thereon, were obtained from one solution. In some trials, electrode 16 was rinsed with deionized water and dried in air, and in others, electrode 16 was not rinsed but allowed to dry in air straight from the cell. In addition, spectra were obtained of the unelectrodeposited solution along with the solution after the electrodeposition. These were prepared by applying ten microliters directly to electrode 16 and drying in air.

The sterilization part of the experiment was done by using an inoculating loop to apply the electrodeposited solution to a culture plate (not shown). These were then incubated at 38° C. overnight. Only *Escherichia coli* was used in the sterilization experiment.

Results

*Escherichia coli*—Spectra

*Escherichia coli* was the most widely studied of all the bacteria. All of the pyrolysis mass spectra obtained were similar using constant deposition voltage. The spectra for *Escherichia coli* are the spectra of FIGS. 2 and 3.

Spectra of FIGS. 4 and 5 are of *Escherichia coli* at four volts in a 20 ml cell with a one milliliter aliquot from the original test tube. The spectra are two sequential samples of the solution. The spectra of FIGS. 6 and 7 are of *Escherichia coli* at five volts for thirty minutes and are consecutive samples. The spectra of FIGS. 8, 9 and 10 are *Escherichia coli* using ten volts for thirty minutes. These latter three spectra were consecutive samples of the same solution.

All of these spectra have the same groupings of peaks and the only major differences are in the intensities. This stands for the grouped spectra and all the spectra put together. The intensities would change with different voltages and different sample times. This suggests that the amount of decomposition differs with different voltage and times. There were very similar spectra which may state a certain period exists during the electrodeposition that the decomposition state may be stable for a while. Perhaps the degree of decomposition is similar at low voltages over time and stabilizes after an initial time at high voltages. The spectra of FIG. 11 is of the solution after the electrodeposition has occurred. It has similar peaks yet different intensities. This suggests that the degree of decomposition in the solution is different than on the wire.

*Escherichia coli*—Sterilization

It was determined that there were live as well as killed bacteria on the wires, electrodes 16 and 18. This was done by first washing the wire in deionized water, then scraping on a culture plate. Growth was seen after one day in the incubator. However, a certain amount of sterilization was observed. This was tested by taking plate tests every thirty minutes during the electrodeposition. After a maximum of 150 minutes, there was not complete sterilization, yet the amount of growth on the plate decreased substantially after each thirty minute test. There was a test at 15 volts, 20 volts, and 20 volts stirred and, in two of the experiments (the 15 volts and 20 volts stirred) after 15 minutes there was a countable number of colonies on the plate. There can be no accurate comparing of methods as to the degree of sterilization because of the ambiguity of the starting concentration of bacteria in the solution.

Wolinella Species

The spectra of FIGS. 12 and 13 are of Wolinella species. The spectra of FIG. 12 is after one hour while the spectra of FIG. 13 is the resultant solution. The spectra of FIGS. 12 and 13 are similar in peaks yet slightly different in intensities suggesting that the bacteria undergoes decomposition as it is electrodeposited on electrode 16.

*Wolinella succinogenes*

The spectra of FIGS. 14, 15 and 16 are consecutive samples of *Wolinella succinogenes* in solution electrodeposited on electrode 16. All three spectra are similar yet different intensities suggesting differences in the degree of decomposition. The spectra of FIG. 17 is of the resultant solution and shows that decomposition is occurring as the bacteria is depositing on electrode 16.

Group B Streptococcus

No real good spectra were obtained using the Group B. Streptococcus. This is not to say that it will not electrodeposit on the wires. There was visual evidence of bacteria on the wires coated with Group B. Streptococcus. There was just no really good run on the pyrolysis mass spectrometer and, in addition, there were not many attempts made. This was because most of the attention was on using the *Escherichia coli*.

In summary, we have found that microorganisms such as *Escherichia coli* and *Wolinella succinogenes*, to name a few, can be electrodeposited on the tip of a wire which can then be used as the electrode for a pyrolysis mass spectrometer. Importantly, the electrodeposition occurs under a weak, direct current voltage and in a relatively short period of time. Advantageously, a fairly rapid determination can be made of the identity of an unknown bacteria species in a liquid using this novel apparatus and method in that it results in the accumulation of a sufficient quantity of bacteria on an electrode. The electrode can then be processed according to conventional techniques in a pyrolysis mass spectrometer where the accumulated bacteria is analyzed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for concentrating biological cells from a liquid medium on an electrode comprising:
   a vessel;
   a liquid medium having biological cells therein in the vessel;
   at least a first electrode and a second electrode immersed in said liquid medium said first electrode having biological cells electrophoretically deposited thereon; and
   electromotive force means for imposing a direct current electromotive force on said liquid medium with said first and second electrodes, said electromotive force concentrating said biological cells on said first electrode, said first electrode comprising a pyrolysis electrode for pyrolyzing said biological cells collected thereon.

2. The apparatus defined in claim 1 wherein said vessel comprises a specimen collection chamber for a liquid medium.

3. The apparatus defined in claim 2 wherein said liquid medium comprises a biological liquid.

4. The apparatus defined in claim 1 wherein said first electrode comprises a Curie point wire for a Curie point mass spectrometer.

5. The apparatus defined in claim 1 wherein said electromotive force means comprises a direct current voltage imposed across said biological cells between said first and second electrodes.

6. The apparatus defined in claim 1 wherein said electromotive force means is used to impart said direct current electromotive force for a time period ranging up to several hours.

7. The apparatus defined in claim 1 wherein said electromotive force means comprises a direct current voltage within the range on the order of up to about 20 volts.

8. An apparatus for concentrating microorganisms from a liquid medium on an electrode comprising:
 a liquid medium having microorganisms suspended therein;
 a pair of electrodes, one of said electrodes comprising an electrode having microorganisms electrophoretically deposited thereon for a Curie point pyrolysis mass spectrometer, said pair of electrodes immersed in the liquid medium; and
 direct current means for imposing a direct current voltage on said liquid medium with said pair of electrodes with said electrode for said Curie point mass spectrometer serving as an anode, said direct current voltage concentrating said microorganisms on said electrode.

9. The apparatus defined in claim 8 wherein said liquid medium comprises a biological liquid.

10. The apparatus defined in claim 8 wherein said direct current means comprises a direct current voltage up to about 20 volts.

11. The apparatus defined in claim 8 wherein said direct current means comprises applying said direct current voltage on said liquid medium for a period of time ranging up to at least two hours.

12. A method for electrodepositing microorganisms on an electrode for subsequent pyrolysis of said microorganisms comprising:
 obtaining a liquid medium having said microorganisms therein;
 selecting at least two electrodes comprising a first electrode and a second electrode, said first electrode comprising an anode;
 immersing a portion of said electrodes in said liquid medium; and
 electrodepositing microorganisms from said liquid medium by imposing a direct current voltage across said electrodes, said microorganisms being deposited on said anode.

13. The method defined in claim 12 wherein said electrodepositing step comprises selecting said anode as a filament for a Curie point pyrolysis mass spectrometer.

14. The method defined in claim 12 wherein said electrodepositing step comprises imposing said direct current voltage for a period of time ranging up to about two hours.

15. The method defined in claim 12 wherein said electrodepositing step comprises imposing said direct current voltage in an amount ranging up to about 20 volts.

* * * * *